(12) United States Patent
Powell et al.

(10) Patent No.: US 8,400,108 B2
(45) Date of Patent: *Mar. 19, 2013

(54) METHOD OF CHARGING AND USING AN ASEPTIC BATTERY ASSEMBLY WITH A REMOVABLE BATTERY PACK

(75) Inventors: Matt Powell, Galesburg, MI (US);
Vaughn R. Gerber, Portage, MI (US);
Ronald Duis, Plainwell, MI (US)

(73) Assignee: Stryker Corporation, Kalamazoo, MI (US)

( * ) Notice: Subject to any disclaimer, the term of this patent is extended or adjusted under 35 U.S.C. 154(b) by 56 days.

This patent is subject to a terminal disclaimer.

(21) Appl. No.: 12/766,267

(22) Filed: Apr. 23, 2010

(65) Prior Publication Data

US 2010/0264876 A1    Oct. 21, 2010

Related U.S. Application Data

(62) Division of application No. 11/341,064, filed on Jan. 27, 2006, now Pat. No. 7,705,559.

(51) Int. Cl.
*H02J 7/00* (2006.01)
(52) U.S. Cl. ..................................... 320/113
(58) Field of Classification Search .................. 320/110, 320/112–115
See application file for complete search history.

(56) References Cited

U.S. PATENT DOCUMENTS

| 4,091,880 A | 5/1978 | Troutner et al. |
| 6,018,227 A | 1/2000 | Kumar et al. |
| 6,059,806 A | 5/2000 | Hoegerle |
| 6,184,655 B1 | 2/2001 | Malackowski |
| 6,917,183 B2 * | 7/2005 | Barlev et al. .................. 320/112 |
| 7,180,760 B2 * | 2/2007 | Varrichio et al. ............... 363/59 |
| 7,705,559 B2 * | 4/2010 | Powell et al. .................. 320/113 |
| 2003/0052729 A1 * | 3/2003 | Hsu et al. ...................... 327/536 |
| 2006/0033442 A1 * | 2/2006 | D'Angelo ....................... 315/86 |
| 2007/0090788 A1 | 4/2007 | Hansford et al. |

FOREIGN PATENT DOCUMENTS

| DE | 19 607 123 A1 | 6/1997 |
| EP | 0 027 959 A1 | 5/1981 |

OTHER PUBLICATIONS

"PCT App. No. PCT/US2007/06027, International Search Report and Written Opinion of the ISA, Jul. 2007".
"Stryker Aseptic Battery and Battery Charger, Photographs, 6 Sheets, Dec. 2004".
"Stryker Aseptic Battery, Photographs, 1 sheet, Dec. 2004".

* cited by examiner

*Primary Examiner* — Jue Zhang

(57) ABSTRACT

A battery assembly with a housing that contains a removable battery pack. The housing, which is sterilzable, has a head designed to couple to a power consuming device. The battery pack, which is not sterlizable, contains at least one rechargeable cell. The battery pack has a head dimensioned to fit the same charger socket that can receive a sterilzable battery. The battery pack has contacts that abut charger contacts. The housing has internal contacts. Collectively, the housing and battery pack are shaped so that, when the battery pack seats in the housing, the battery pack contacts abut the housing internal contacts. The housing internal contacts are connected to the housing external contacts for supply power to the power consuming device. A cover selectively holds the battery pack in the housing chamber.

12 Claims, 12 Drawing Sheets

METHOD OF CHARGING AND USING AN ASEPTIC BATTERY ASSEMBLY WITH A REMOVABLE BATTERY PACK

RELATIONSHIP TO EARLIER FILED APPLICATION

This application is a divisional of U.S. patent application Ser. No. 11/341,064 filed 27 Jan. 2006 now U.S. Pat. No. 7,705,559 the contents of which is explicitly incorporated herein by reference.

FIELD OF THE INVENTION

This invention is generally related to rechargeable aseptic battery assembly. More particularly, this invention is related to an aseptic battery assembly with a removable cell cluster that is simple to use.

BACKGROUND OF THE INVENTION

A battery often energizes a powered surgical tool used in an operating room to perform a surgical procedure. The use of a battery eliminates the need to provide a power cord connected to an external power source. The elimination of the power cord offers several benefits over corded surgical tools. Surgical personnel using this type of tool do not have to concern themselves with either sterilizing a cord so that it can be brought into the sterile surgical field surrounding the patient or ensuring that, during surgery, an unsterilized cord is not inadvertently introduced into the sterile field. Moreover, the elimination of the cord results in the like elimination of the physical clutter and field-of-view blockage the cord otherwise brings to a surgical procedure.

In an operating room, batteries are used to power more than the tools used to perform the surgical procedure. Batteries are also used to energize the power consuming components integral with a personal protection system surgical personnel sometimes wear when performing a procedure. This system typically includes some type of hooded garment. Internal to the garment is a ventilation unit for circulating air within the garment. Some of these systems also have lights for illuminating the surgical site or radios that facilitate conventional spoken level conversation with other persons involved in performing the procedure. Each of these units, the ventilation unit, the light unit and the radio, requires a source of power. By providing this power from the battery, the need to attach cords to each individual wearing such a unit is eliminated. This reduces number of cords in the operating room personnel would otherwise have to avoid. Further, eliminating these cords likewise eliminates the restrictions of movement they place on the individual using the system.

Many batteries used in the operating room include rechargeable cells. This allows the battery to be repetitively used. Typically, the cells are bound together to form a cell cluster.

To reduce, if not eliminate, the possibility of patient infection, it is necessary to sterilize any object introduced into the sterile field. (Generally, the "sterile field" is the space surrounding the surgical site at which the procedure is performed. The sterile field extends to the front of the surgeon and assisting personnel.) This requirement extends to the batteries used to charge surgical tools employed to perform the procedure. Typically, a battery is sterilized by placement in an autoclave. In the autoclave, the battery is subjected to an atmosphere saturated with water vapor (steam), the temperature is approximately 270° F. and the atmospheric pressure is approximately 30 psi (Gage).

One disadvantage of the above process is that exposure to the heat in the autoclave damages the cells. This is especially true if the battery is autoclaved for time periods of 10 minutes or more. Some sterilization protocols require batteries for this period of time, if not longer.

To prevent autoclave-induced cell damage, some batteries are provided with removable cell clusters. This type of battery includes a housing with a void space for accommodating the cells. The housing also includes a moveable cover that encloses the cells in the void space. This allows the cell cluster to be removed from the housing prior to the autoclave process. Once the housing is sterilized and cells charged, the cluster is fitted into the housing. Once the process is complete, the surgical personnel have available for use a fully charged and autoclaved sterilized battery.

The above batteries perform reasonably in that they provide charges to devices that are used in sterile environments. However, the known batteries tend to be large in size. This reduces the ergonomics associated with working with these batteries. Further, the cell clusters internal to these batteries are often known to require custom fixtures of sockets for attaching them to the complementary chargers to which they are fitted. The Applicants' Assignee's U.S. Patent No. Applicant's U.S. Pat. No. 6,018,227, BATTERY CHARGER ESPECIALLY USEFUL WITH STERILIZABLE RECHARGEABLE BATTERY PACKS, issued Jan. 25, 2000 and incorporated herein by reference, discloses that it is possible to provide a charger with separate socket-forming modules for use with different types of battery assemblies. Thus, the known systems require the entity supplying the charger, and sometimes the facility using the batteries, to maintain a supply of chargers or modules with different shaped sockets.

SUMMARY OF THE INVENTION

This invention relates to a new and useful aseptic battery assembly. The aseptic battery of this assembly includes a battery pack that does not add to the overhead of providing the battery assembly. The aseptic battery assembly of this invention further includes a housing that is relatively small in size.

More particularly, the aseptic battery assembly of this invention includes a housing that can withstand the rigors of sterilization. A battery pack, that is typically not sterilzable, contains one or more rechargeable cells is removably and releasably seated in the housing. The housing and battery pack each have a head. The heads are the structural members of the housing and battery pack through which charge is both stored in and withdrawn from the cells. The head of the battery pack is shaped to be received in the socket of a complementary charger designed to receive the head of a battery able to withstand the rigors of sterilization. When the battery pack is so seated, the charger is able to charge it as if the pack is a sterilzable battery.

The housing of the battery assembly of this invention is also provided with a seal between the housing body and the cover that encloses the battery pack. The seal is compressed between the inner edges of the housing panels and the cover. This construction minimizes the dimensions of these panels so as to, in turn, hold the overall size, length and width, of the housing to a minimum.

BRIEF DESCRIPTION OF THE DRAWINGS

The invention is pointed out with particularity in the claims. The above and further features and benefits of this invention are better understood by the following Detailed Description taken in conjunction with the accompanying drawings in which:

DETAILED DESCRIPTION

Figure 1:
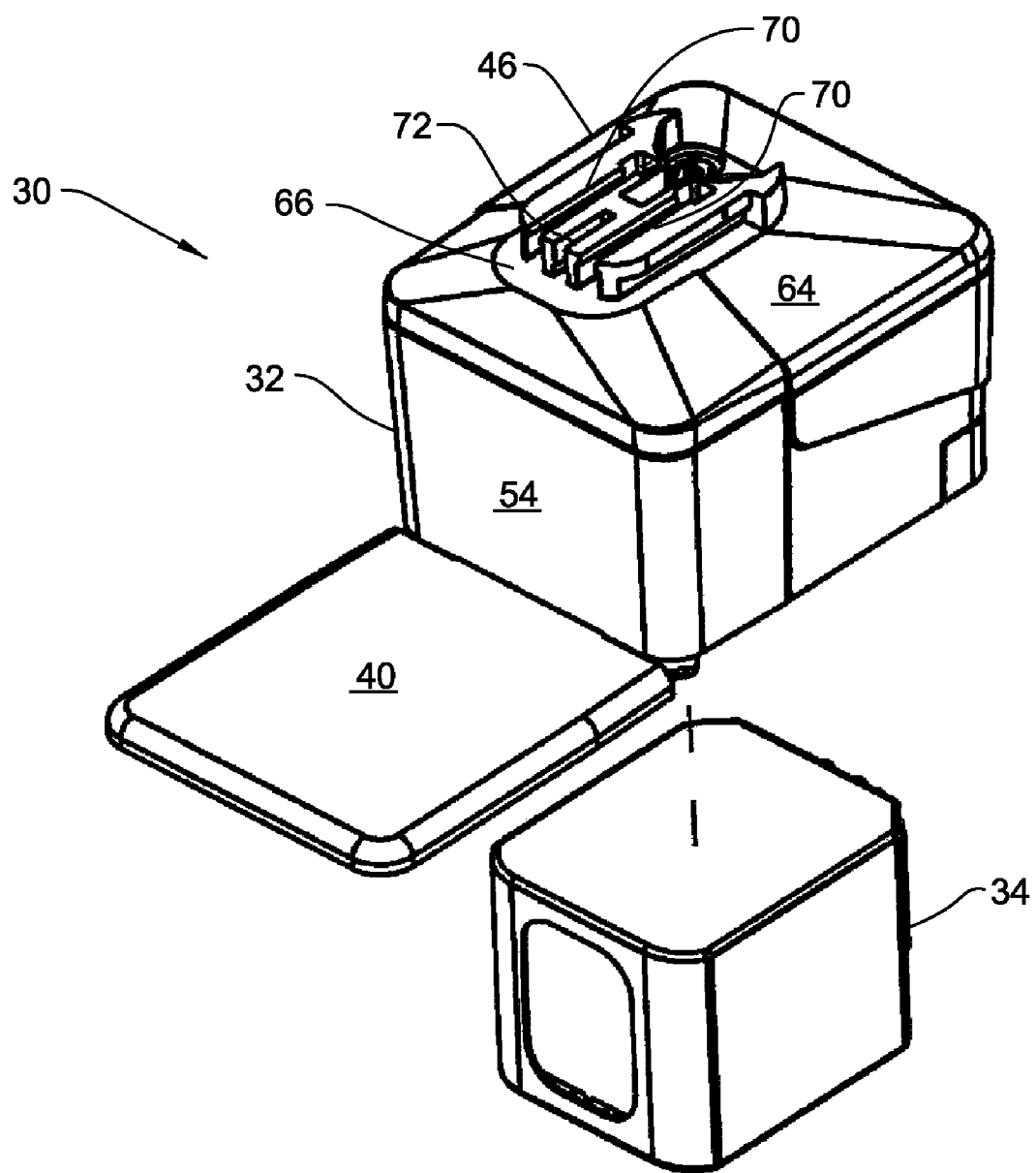
FIG. 1 is a top exploded view of the battery assembly of this invention.
Figure 2:
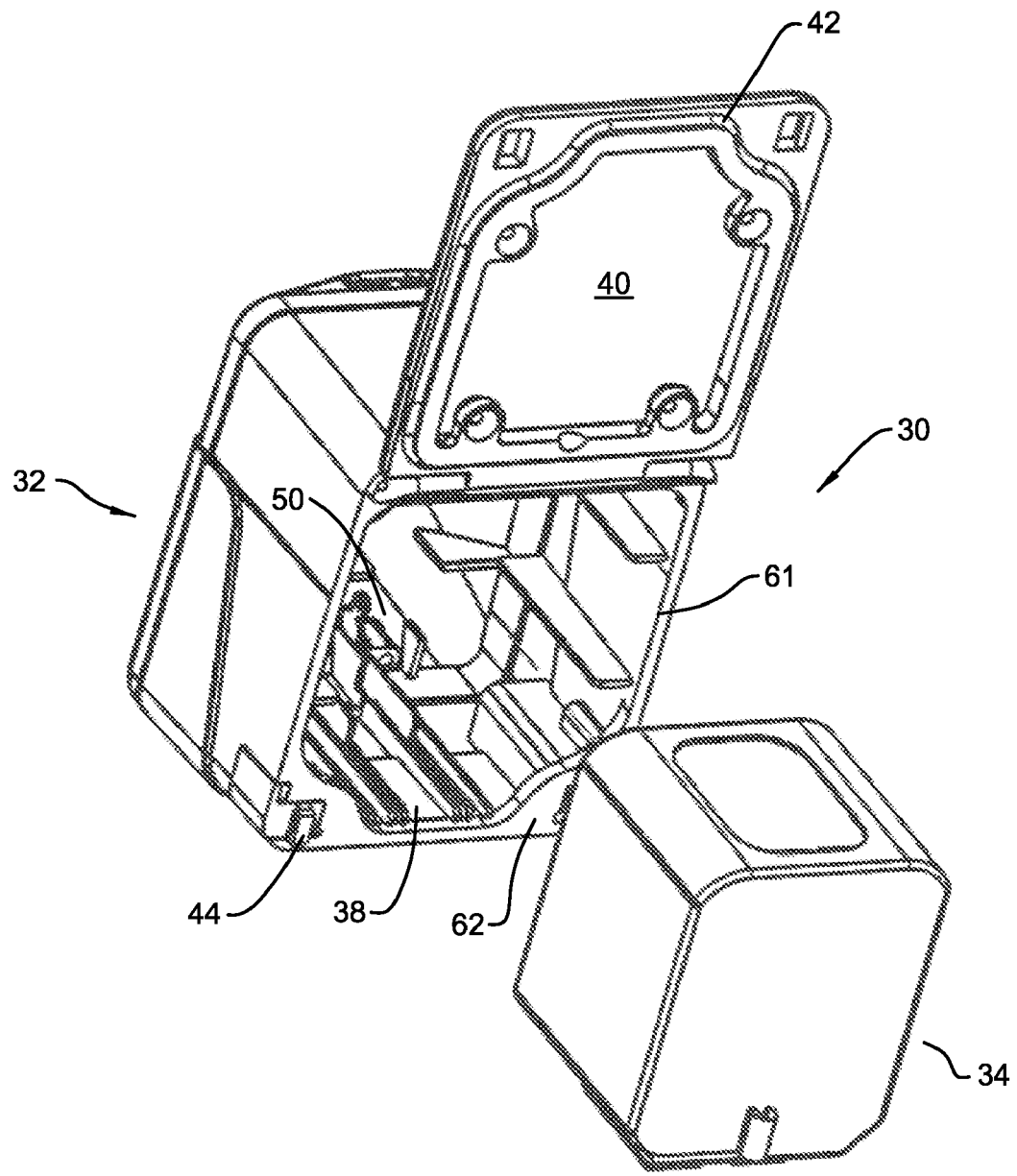
FIG. 2 is a bottom exploded view of battery assembly.
Figure 3:
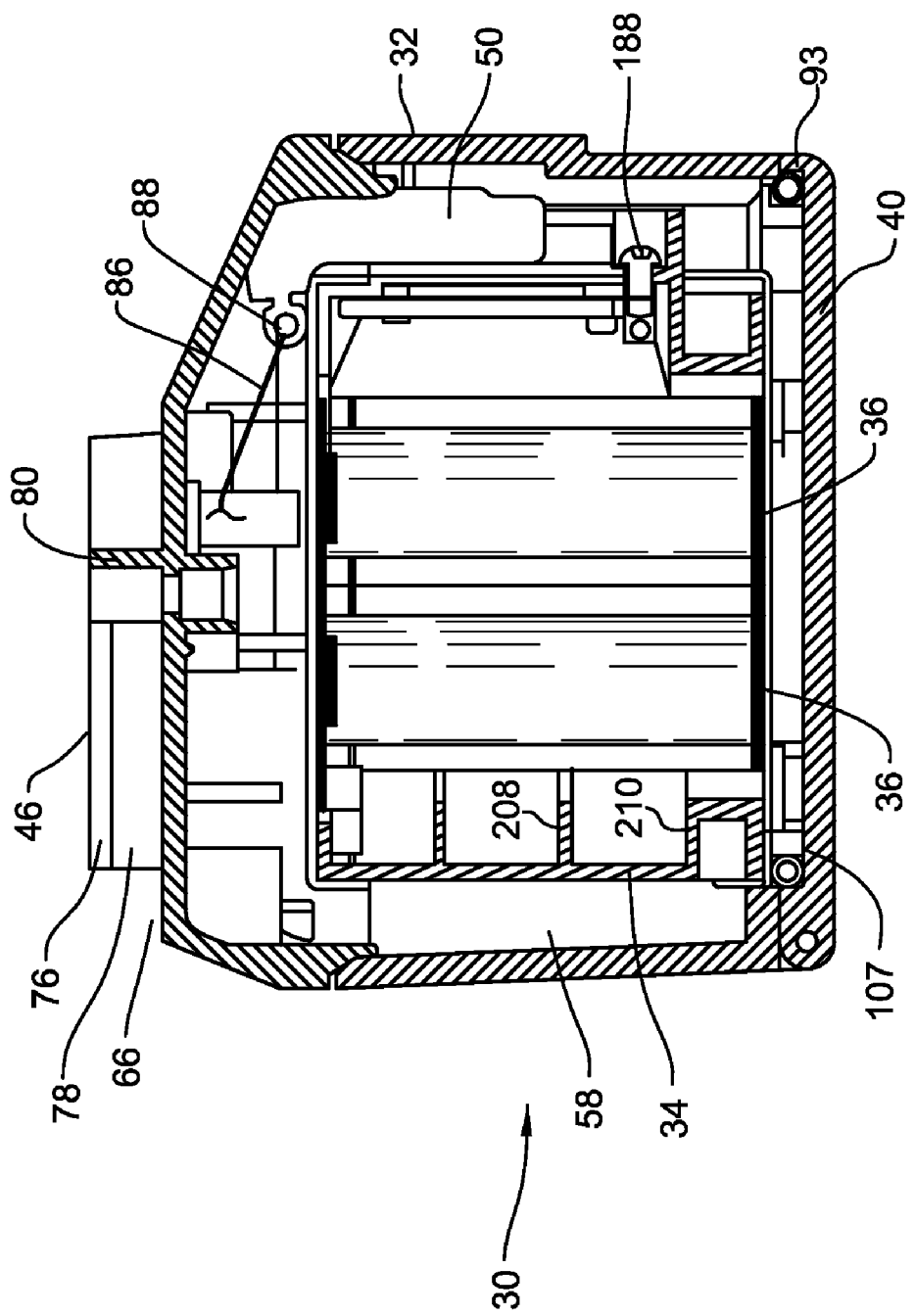
FIG. 3 is sectional view through the battery assembly, front to back.

FIGS. 1-3 illustrate the basic components of the battery assembly 30 of this invention. Specifically, battery assembly 30 includes a housing 32 in which a battery pack 34 is removably seated. Battery pack 34 includes a number of rechargeable cells 36 for storing electrical energy, charge. Housing 32 defines a chamber 38 in which the battery pack 34 is disposed. A cover 40 pivotally mounted to the rest of the housing 32 forms the base of the housing and, when closed, covers the chamber 38. A seal 42 is mounted to the cover 40. When cover 40 is closed, seal 42 presses around the adjacent chamber-defining panels of the housing 32 to form a barrier between the cover and the rest of the housing. Latches 44 mounted to the housing releasably hold the cover in the closed position.

Figure 12:
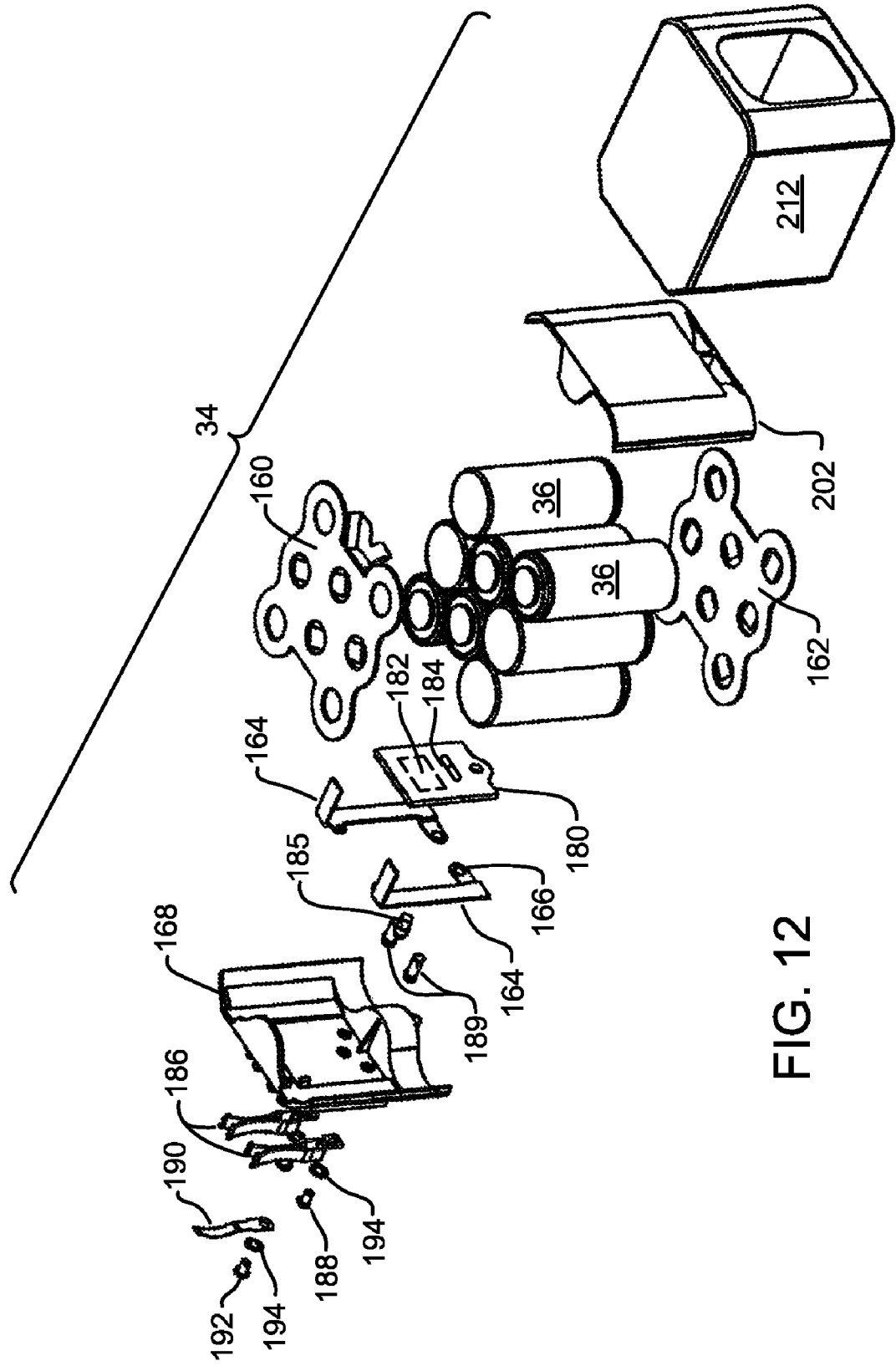
FIG. 12 is an exploded view of the components forming the battery pack.

The housing 32 and battery pack 34 are each provided with separate heads 46 and 48, respectively, (battery pack head best seen in FIG. 12.) As described below mounted to the individual housing and battery pack heads 46 and 48, respectively, are contacts through which charge is supplied to and power drawn from the cells 36. Internal to the housing 32 are blade contacts 50. The blade contacts 50 are connected to the complementary contacts in the housing head 46. The blade contacts 50 project into the housing chamber 38 so that, when the battery pack 34 is seated in the chamber, the blade contacts 50 abut the battery pack contacts.

Figure 4:
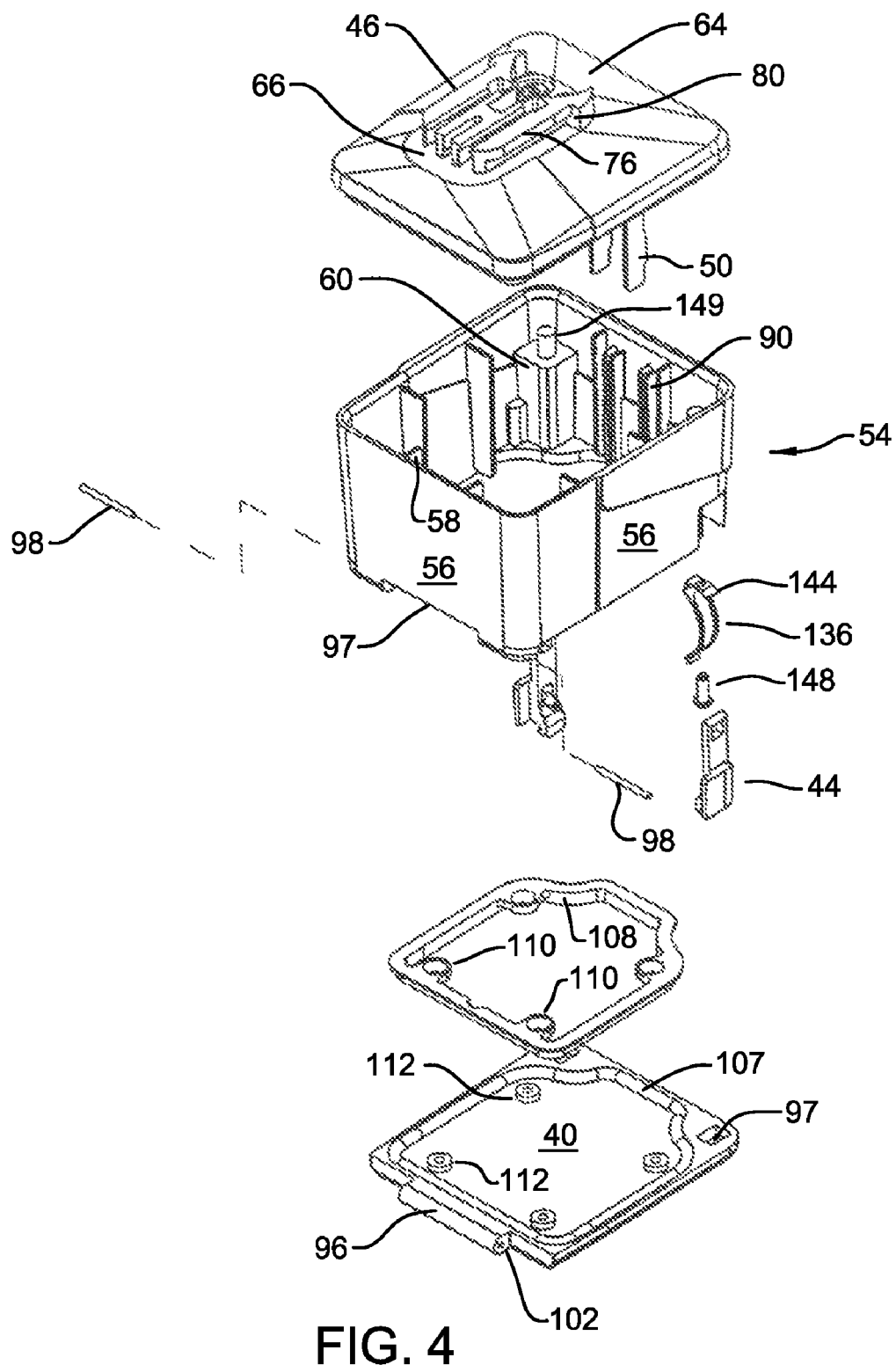
FIG. 4 is an exploded view of the components forming the housing of the battery assembly.
Figure 5:
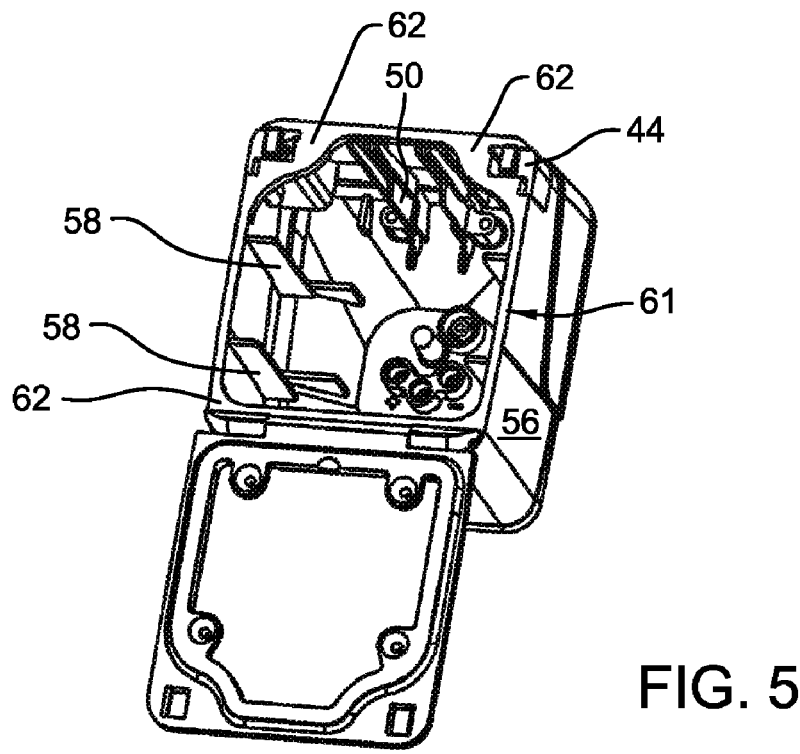
FIG. 5 is a perspective view of the battery housing illustrating the inside of the housing.
Figure 6:
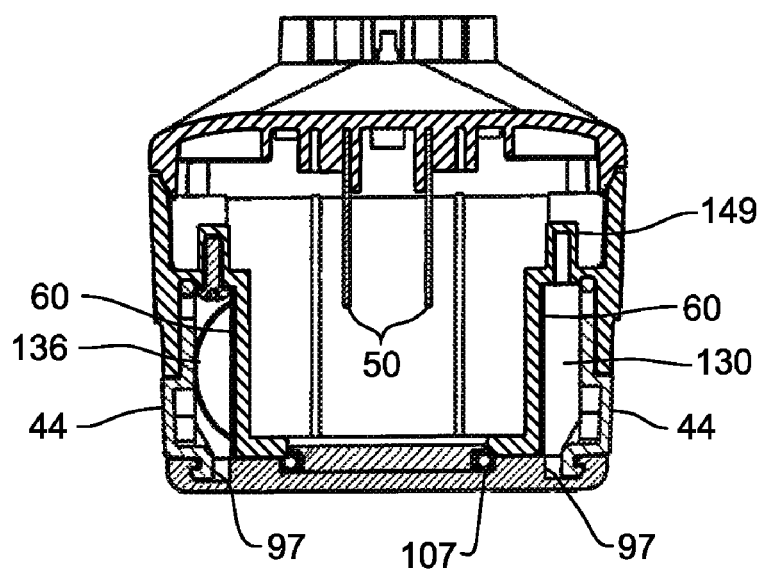
FIG. 6 is a cross sectional view of the housing illustrating how the latches hold the cover in the closed position.

Referring now to FIGS. 4 and 5, the construction of housing 32, which is formed from material that is sterilizable, is now described. The housing 32 is formed to have a body 54 that includes four panels 56 formed together as a single, generally rectangular unit. The inner surfaces of panels 56 collectively define the perimeter of housing chamber 38. Housing body 54 is further formed so that ribs 58 formed integrally with the panels 56 extend from the inner surfaces of panels into the chamber 38. When the battery pack 34 is seated in the housing chamber 38, ribs 58 prevent side-to-side movement of the pack.

The housing body 54 is further formed have two rectangular blocks 60. Blocks 60 are located adjacent the insides of the corners between panels 56 at one end of the housing body 54. As discussed below, blocks 60 define void spaces in which latches 44 are fitted.

At the bottom end thereof, housing body 54 has an inner edge 61. Along the most of the front and side panels, edge 61 is the actual inner edge surface of the panel. At the corners where the panels 56 meet, the housing is formed with reinforcing flanges 62. The inner perimeters of the flanges 62 form corner portions of abutting edges 61.

A lid 64 is disposed over the housing body 54 so as to form the top of the housing 32. Lid 64 has four inwardly tapered panels (not identified). The tapered panels meet at a planar horizontal surface 66. Battery housing head 46 projects upwardly from surface 66. The head 46, which is formed integrally with the lid, is the form of a solid plastic member. The head 46, seen best in FIGS. 1 and 4, is generally rectangularly shaped and longer front-to-back than side-to-side.

Housing head 46 is provided with geometric features to facilitate the coupling of the head both to a charger and the surgical tool the battery assembly 30 is employed to power. In the illustrated version of the invention, these features include two slots 70 that extend inwardly from the forward end of the head 46. Slots 70 are located on either side of the longitudinal centerline of the head 46. Housing head 46 is further formed so that at each slot 70 has a base with a width greater than that of the more forward portions of the slot, (base not identified). A constant width slot 72 is located between the slots 70. More particularly, battery housing head 46 is formed so that slot 72 is centered on and extends along the longitudinal axis of the head. Slot 72 extends through the housing head 46.

The rear face of housing head 46 extends inwardly to expose a section of lid horizontal surface 66. A latch, similar to latch 232 of a sterilizable battery 224 (FIG. 19), the exact structure of which is not part of this invention, is moveably mounted to the head 46 so as to be located adjacent the rear face. The latch is the structural member of the battery housing 32 that releasably holds battery assembly 30 and, more particularly, head 46, to the device the battery is used to power. It should be clear that the presence of latch is optional and may not be present in all versions of the invention.

Battery housing head 46 is further formed to have opposed lips 76 that extend outwardly along the top of the head along the longitudinal sides of the head. In the described version of the invention, lips 76 are longer than slots 70. Each lip 76 and the opposed spaced portion of the lid horizontal surface 66 thus define a slot 78. Rearward of each lip 76, the head is formed to have solid finger 80. The front facing surfaces of the fingers 80 thus define the rear base ends of the adjacent slots 78. The opposed rear facing surfaces of the fingers 80 are the rear face of the head 46 that define where the latch is seated.

Figure 7:
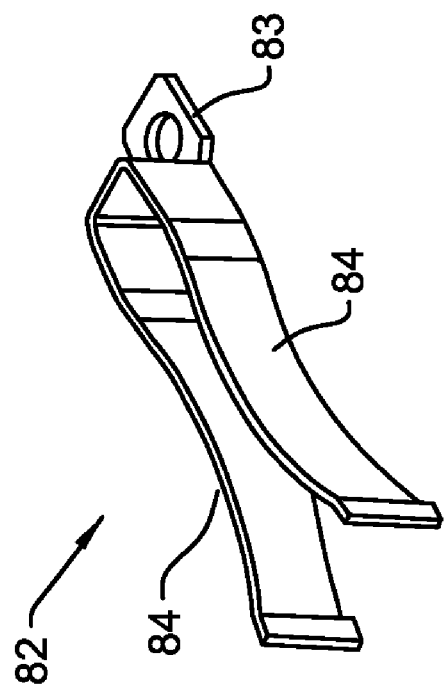
FIG. 7 is a perspective view of one of the contacts employed as the external contact of the housing and the external contact of the battery pack.
Figure 10:
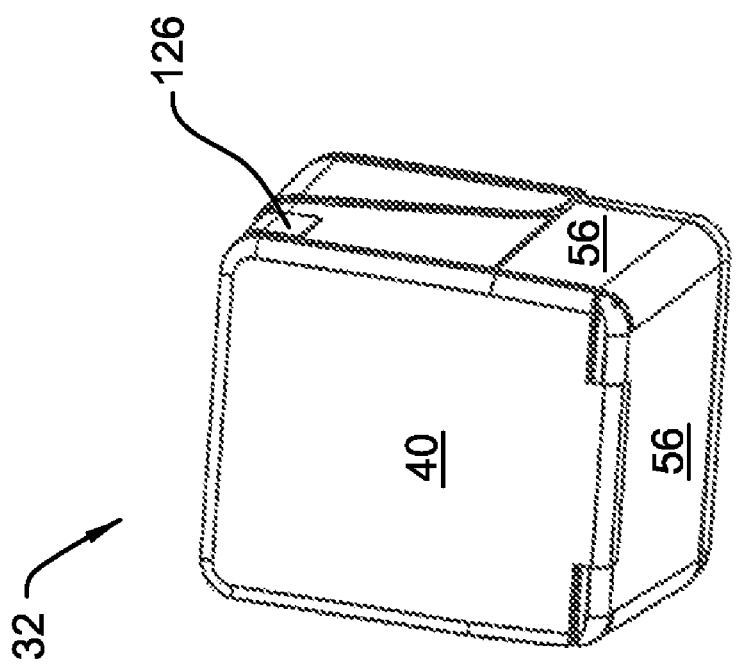
FIG. 10 is a perspective view of the bottom of the housing when the cover is in the closed position.

A contact 82, seen in FIG. 7, is seated in each of the slots 70. Contacts 82 are the members through which energy from the charger can be stored in the cells and through which energy is supplied to power the tool to which the battery is attached. Each contact includes a flat base 83. The contact base 83 is formed with a through hole, (hole not identified). The hole receives a conductive fastener, not illustrated, that secures the contact to the housing head 46. Two symmetric, inwardly bowed opposed legs 84 extend from the base 83. Each contact 82 is seated in the associated slot 70 so that legs 84 are in the elongated section and the base 83 is in the wide diameter base end.

Lid 64 is welded to housing body 54 to form a unitary structure. One process for welding these components together so as to form a seamless bond therebetween is disclosed in the Applicants' Assignee's U.S. Patent Application No. 60/729,338, SYSTEM AND METHOD FOR RECHARGING A BATTERY EXPOSED TO A HARSH ENVIRONMENT, filed Oct. 21, 2005, the contents of which are published in U.S. Pat. Pub. No. US 2007/0090788 incorporated herein by reference.

Blade contacts 50 are now described by reference to FIGS. 4, and 5, is also mounted to the housing. Each blade contact 50 is electrically connected to a separate one of the exposed housing contacts 82. Each blade contact 50 is generally in the form of a flat piece of conductive metal. The top end of the contact 50 is formed with eye-loops 88. The eye-hole 88 is provided to receive a wire 86 that extends from blade contact to the conductive fastener that holds the associated head contact 82 to the housing 32. More particularly, while not shown, it should be understood that wire 86 extends to a conductive plug internal to the housing lid 64 that receives the fastener.

Figure 18:
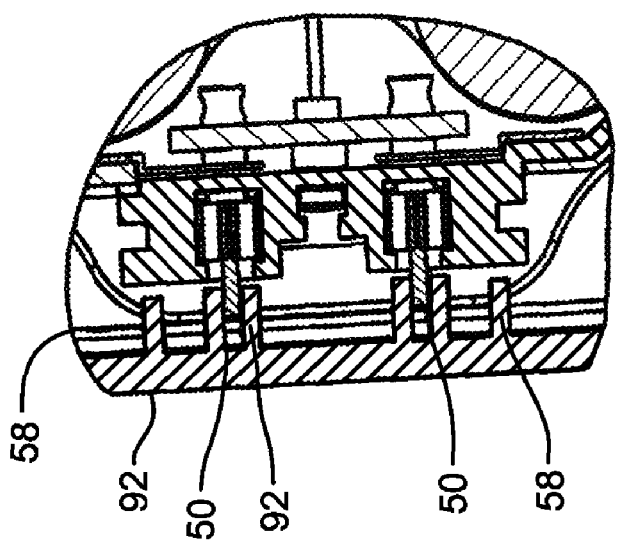
FIG. 18 is an enlargement of the portion of the view of FIG. 17 illustrating the connection established by the housing blade contacts with the complementary battery pack contacts.

The head end of each blade contact is compression fit between two opposed webs 90, one seen in FIG. 5, that extend downwardly from the inner surface of the rear facing tapered panel of lid 64 (one web 90 shown). The webs 90 are dimensioned so that contact eye-loops 88 extend inwardly from the webs. The outer facing perimeter of each blade contact 50, along the length of the contact is further seated between two parallel spaced apart webs 92 integral with the housing body 54. Webs 92, seen best in FIG. 18, project inwardly from the inner surface of the rearward facing housing panel 56. When housing 54 is assembled as part of the process of fitting the lid 64 to the body 54, each blade contact 50 is seated tightly between the associated pair of webs 92.

Figure 11:
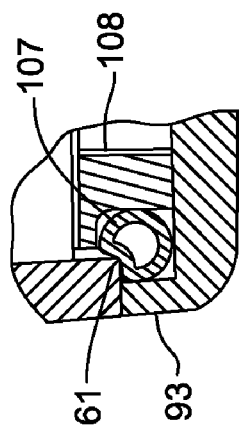
FIG. 11 is a cross-sectional view of the bottom of the housing when the cover is in the closed position.

As seen best in FIGS. 3 and 4, the housing cover 40 is generally in the form of a rectangular panel. Along the inner surface of the cover 40, there is an inwardly extending lip 93. The cover 40 is shaped so that the outer surface of the lip 93 is, when the cover is closed, flush with outer surface of the housing body 54. Along the straight portions of the perimeter of the cover 40, lip 93 has a thickness less than that of the adjacent housing panels 56. The inner horizontal surface of lip 93 is spaced slightly outwardly of housing body inner edge 61, as illustrated in FIG. 11. In some versions of the invention, this distance is 0.010 inches or more and, more preferred versions of the invention 0.030 inches or more.

Cover 40 is further formed to have a rib 96 that projects outwardly from the front edge of the cover. When the housing 32 is assembled, rib 96 seats in a slot 97 formed in the adjacent base panel 56. Two pins 98 pivotally hold the cover 40 to the rest of the housing 32. Pins 98 seat in openings formed in the base panel (base panel openings not illustrated and a bore 102 formed in rib 96.

Housing cover 40 is further formed so that the sections adjacent the corners spaced from rib 96 are of a slightly greater thickness than the center of the cover. One closed-end opening 97 is formed in each of these sections. Each opening 97 is positioned to receive a complementary one of the latches 44. The covers are further formed so that a horizontally extending tab 99 flush with the adjacent portion of the cover extends over each opening 97 to partially cover the opening.

A continuous seal 107 is secured to the inwardly facing surface of cover 40. The seal 107 is formed from a tubular material that is compressible and sterlizable. Suitable materials from which seal 107 can be formed include EPDM rubber or silicone rubber. Seal 107 is disposed around the inner wall of cover lip 93. The seal 107 is so as to have a diameter that results in the seal projecting above the cover lip 93 and so that the center of the seal, when viewed in cross section is located inwardly of the housing body inner edge 61.

A retainer 108 disposed over the inner surface of cover 40 holds the seal 107 to the cover. Retainer 108 is generally in the form of a closed structure that has L-shaped cross sectional profile. More particularly, the vertical section of the retainer is located inwardly of the cover lip 93. The vertical section of the retainer 108 is further shaped to have a height greater than that of the cover lip. The horizontal section of the retainer 108 extends outwardly towards the lip so as to extend over the seal 107. The retainer 108 is shaped so that when the cover 40 is closed, there is a gap of 0.060 inches or less between the inner surface of the housing body panels 56 and the outer perimeter of the horizontal extending portion of the retainer and, more preferably, 0.030 inches or less. Thus, as seen in FIG. 11, upon assembly, seal 107 is sandwiched between the cover lip 93 and retainer 108.

Threaded fasteners, not illustrated, secure retainer 108 to cover 40. The fasteners extend through inwardly extending tabs 110 integral with the retainer 108. The fasteners seat in bores 112 formed in the cover 40.

Figure 8:
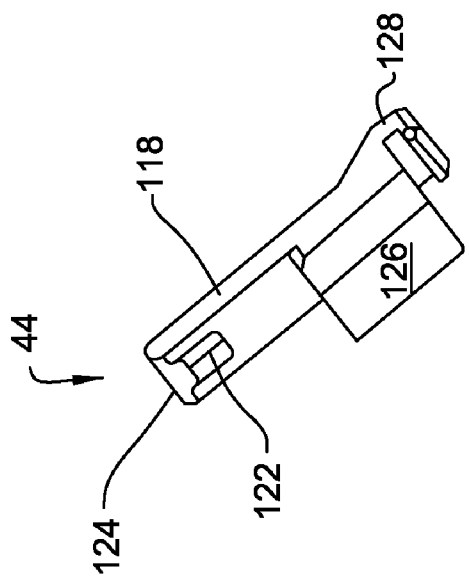
FIG. 8 is a perspective view of the latch.

Two latches 44, one which is now described in detail with respect to FIG. 8, releasably hold the cover 40 in the closed position. Each latch 44 is formed with an elongated body 118 that has a generally rectangular cross sectional profile. The latch body 118 is formed to have a laterally extending opening 122. Latch body 118 is also shaped so that the bottom of the body, the portion that forms the bottom perimeter of opening 122 is generally in the form of a rod 124. Latch 44 is further formed so as to have rectangular shaped shoulder 126 that projects outwardly from one side of the latch body 118.

Above shoulder 126, the latch 44 is shaped to have a head 128. Latch head 128 is generally J-shaped such that head has a hook that is parallel with the top of the shoulder 126.

Figure 9:
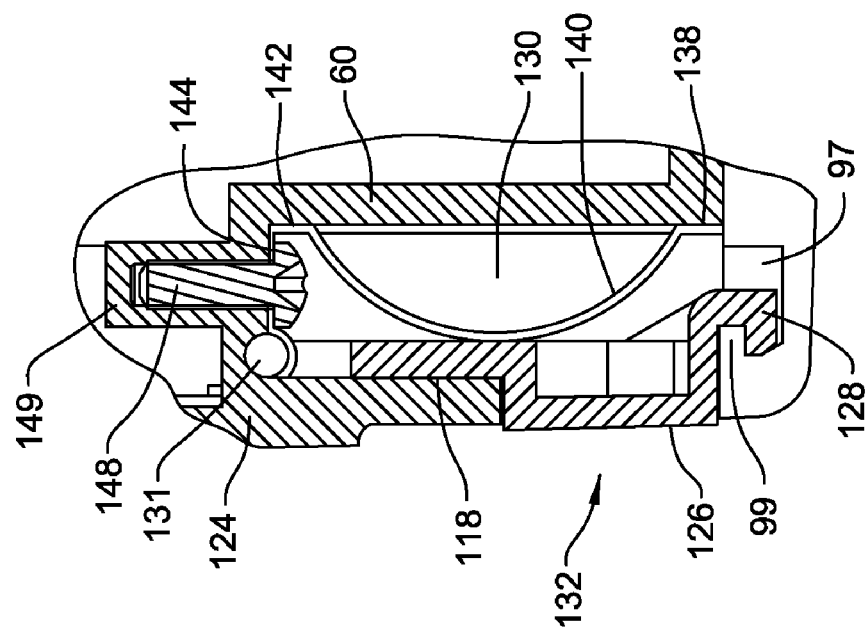
FIG. 9 is an enlarged cross section illustrating how a single latch holds the cover in the closed position.

FIG. 9 depicts how a latch 44 is moveably secured in a rectangular bore 130 formed in one of the housing base blocks 60. The base side panel 56 adjacent each block is formed with a cut out 132 contiguous with the bore 130. When the latch 44 is seated in the block bore 130, the latch shoulder 126 seats in the space defined by panel cut out 132. Housing base 54 is further formed so that the section of each block 60 that defines bore 130 defines a groove 131 at the base of the bore. Groove 131 is dimensioned to receive the latch rod shaped section 124.

A spring 136 disposed in each block bore 130 both holds the latch 44 in the bore and biases the latch into the locked position. The spring 136 is formed from flexible metal has first and second coplanar flat sections 138 and 142 that are separated by a bowed section 140. A foot 144 extends perpendicularly from in the topmost flat section, section 142 in FIG. 9. The outer end of foot 144 has a curved profile that allows the foot to be fitted over the rod shaped section 124 of the latch 44.

At assembly, the latch 44 and spring 136 are seated in the outer portion of block bore 130. Initially, the spring is positioned so that the outer curved end of the foot 144 seats over latch rod shaped section 124. The sub-assembly is placed in the block bore 130 so that the bottom of the latch rod shaped section 124 seats in the groove 131. As consequence of the fitting of this sub assembly in the bore 130, spring flat sections 138 and 142 seat against the inner surface of block 60 that defines the inner perimeter of bore 130. Bow section 140 presses against latch body 118. Spring foot 144 both seats against the base of bore 130 and extends over latch rod section 124.

A fastener 148 extends through an opening in the spring foot 144 into a bore formed in a post 149 integral with each block 60, (spring opening and post bore not identified.) The fastener thus holds spring 136 and, by extension, the latch 44 in the block bore 130. The force exerted by the spring bow 140 holds the latch 44 in the outward, latched position.

When the housing cover 40 is closed over the open end of housing body 54, each latch head 128 seats in a complementary one of the cover openings 97. More particular, the latch head 128 serves as a female member for receiving the cover tab 99 that projects partially over the opening.

The basic structure of the battery pack 34, which cannot withstand the rigors of sterilization, is now described by reference to FIG. 12. The rechargeable cells 36 are packaged together. Top and bottom binders 160 and 162, respectively, both physically hold the cells together as a single unit and provide electrical connections between the cells. The incorporated by reference U.S. Pat. App. No. 60/729,338 describes the structure of the binders 160 and 162 and how an automated process is used to assemble the cells 36 and binders into a single unit referred to as the cell cluster.

The above-cited application also described why the cells are packed together so that each cell forms at least a portion of the outer perimeter of the cell cluster. For the purposes of this application sufficient to note that the two cells 36 of the center row are located inwardly of the three cell sets forming the two outer rows. It should of course be recognized this invention is not limited to any number of cells, at least one cells, or any particular arrangement of plural cells.

Planar metal members bent into an L-shape form the internal contacts 164 of the battery pack 34. The relative short section of the two internal contacts 164 are welded, soldered or otherwise permanently secured to separate terminals of the cells 36. Each internal contact 164 is further formed so that at the end opposite the end connected to the cell cluster there is a tab 166 formed with an opening (opening not identified).

Figure 13:
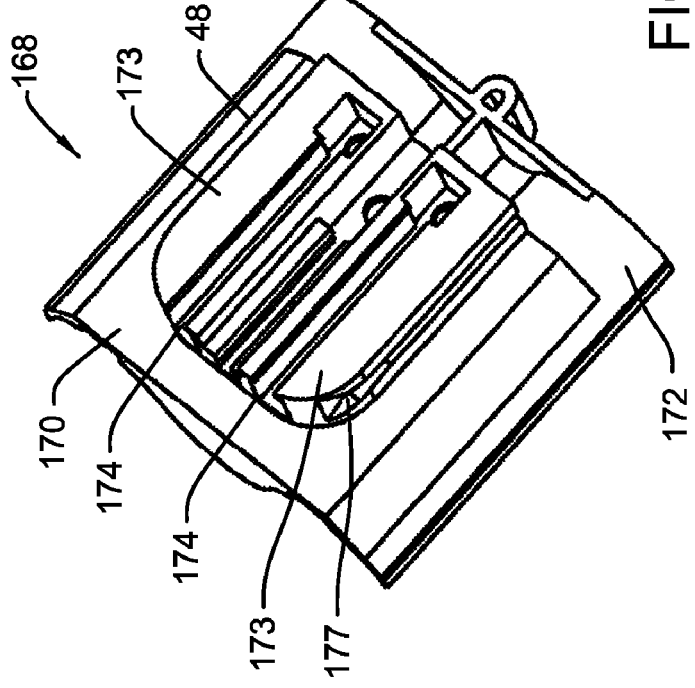
FIG. 13 is a top perspective view of the top plate of the battery pack.

A front plate 168 is disposed over the internal contacts 164 and the adjacent side of the cell cluster. As seen in FIGS. 12 and 13, front plate 168 is formed to have a generally planar base 170. Curved wings 172 extend from the lateral side edges of the base 170. The front plate 168 is dimensioned so that each wing 172 curves partially over the adjacent cell 36 of the adjacent outer row of cells.

Figure 14:
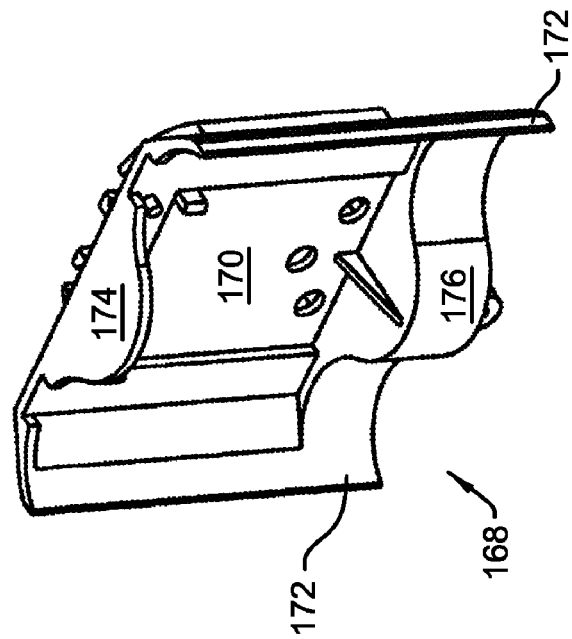
FIG. 14 is a bottom perspective view of the top plate of the battery pack.

Front plate 168 is further shaped so that two convex ribs 174 and 176 extend outwardly from the undersurface of the base 170. One rib adjacent, rib 174 in FIG. 14 adjacent one end of the front plate 168, is relatively thin. The second rib, rib 176 adjacent the opposed end of the front plate 168 is relatively thick. When battery pack 34 is assembled, both ribs 174 and 176 seat in the void space between the outer rows of the cells 36, in the space immediately forward the center row of the cells.

Figure 19:
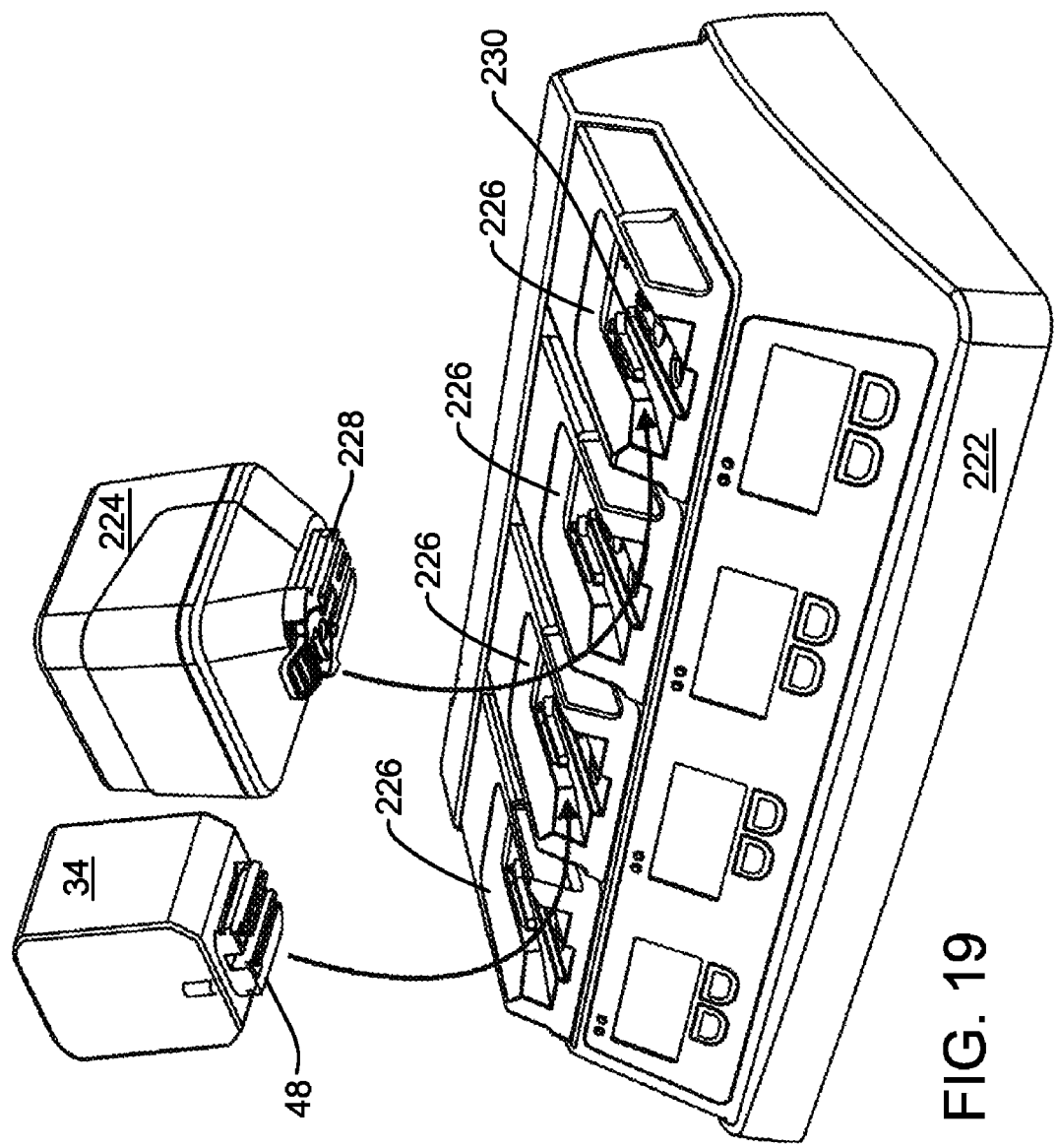
FIG. 19 illustrates how a battery pack of this invention fits in a charger socket dimensioned to receive a sterilizable battery.

Battery pack head 48 is integrally formed with the front plate 168 and exposed the plate base 170. Battery pack head 48 has the geometric features that allow head 48 to be fitted to the same charger socket to which housing head 46 can be attached. Battery pack head 48, as discussed below by reference to FIG. 19, is further formed to have geometric features that allow head 48 to be fitted to the same charger socket 226 that can also receive the head of a sterilizable battery 224. However, battery pack head 48 does not have a latch for holding the battery pack to the device the pack is intended to power. In the illustrated version of the invention, head 48 has two symmetric spaced apart islands 173. Islands 173 are located equidistantly apart from the longitudinal axis of the front plate 168. Each island 173 is formed with a slot 174. Each slot 174 has a geometry essentially identical to that of the geometry of the slots 70 of housing head 46. The outer lateral edge of each island 173 is formed with a slot 177 that projects laterally outwardly. In the illustrated version of the invention slots 177 (one shown) are geometric features of the battery pack head 48 that allow it to be fit in the charger socket designed to receive housing head 46. Each slot 177 thus performs the same function as a housing head lip 76 in relationship to the charger.

Returning to FIG. 12, it can be seen that the battery pack 34 also contains a circuit board 180. Circuit board 180 supports a microcontroller 182 (shown as a phantom block) and a temperature sensor 184. In the Figures, the temperature sensor 184 is shown as facing toward the cells 36. This is so the temperature sensor 184, as closely as possible, generates an output signal representative of the temperature of the cells 36. As described in the above cited incorporated by reference U.S. Pat. No. 6,018,227 and U.S. Pat. App. Ser. No. 60/729, 338, and also U.S. Pat. No. and U.S. Pat. No. 6,184,655, BATTERY CHARGE SYSTEM WITH INTERNAL POWER MANAGER, issued Feb. 5 2001, also incorporated herein by reference, microcontroller 182 contains instruction data used by a charger to regulate the charging of the cells and data that describes the charge, use and sterilization history of the battery pack 34.

The temperature sensor 184 typically outputs its temperature-variable signal to the microcontroller 182. The temperature data obtained from sensor 184 is stored in the microcontroller 182 as history data and/or used as input variable by the charger to regulate the charging sequence. The temperature data may also be used by the tool the battery assembly 30 is used to power to evaluate whether or not the assembly is functioning properly.

A post 185 formed from conductive material suspends the circuit board 180 below the front plate base 170. A solder connection between the post and a conductive trace on the printed circuit board establishes a one-wire communications path, (trace and solder joint not shown.) In some versions of the invention, front plate 168 is formed with a structural member that holds the circuit board 180 away from the surface of the plate base 170. This structural member can, for example, be a tab (not illustrated) that extend from one of the ribs 174 or 176 over the plate base 170.

An external contact 186 is disposed in each slot 174. Contacts 186 are identical to contacts 82 of battery housing 32. A screw 188 formed from conductive material holds contact 186 in the associated slot 174. (Not identified are the through holes in the front plate base 170 through which screws 188 extend. More particularly, the screw is screwed into a plug 189 that is clearance fit into the opening integral with the base through which the associated screw extends. Plugs 189 extend beyond the inner surface of the front plate 168. Each plug 189 is seated in the opening of the tab 166 of an associated internal contact 164. More particularly, each plug 189 is soldered or welded in the tab opening. Thus, the screw securing of each external contact 186 to the battery pack front plate 168 also results in an electrical connection being established between the external contact 186 and an associated one of the internal contacts 164.

A communications contact 190 is also disposed within the battery pack head 48. More particularly, the communications contact 190 is disposed between islands 173. While not specifically identified, it can be seen that communications contact 190 includes a main body that is outwardly bowed and a tail with an eye-opening. A conductive screw 192 that extends through the contact eye-opening holds contact 190 to the front plate 168. More particularly, screw 192 seats in a bore internal to post 185. Thus, screw 192 also provides a conductive connection between contact 190 and the one wire conductor or the printed circuit board 180. In FIG. 12 lock washers 194 are shown around screws 188 and 192.

Figure 16:
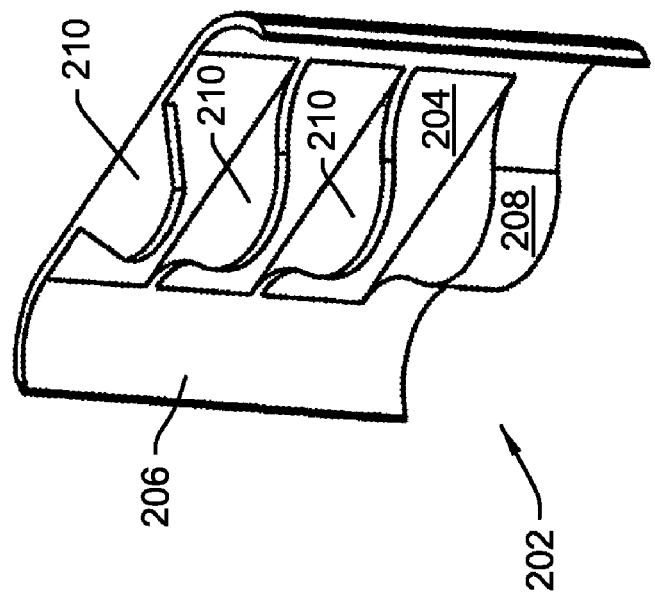
FIG. 16 is a bottom perspective view of the bottom plate of the battery pack.
Figure 15:
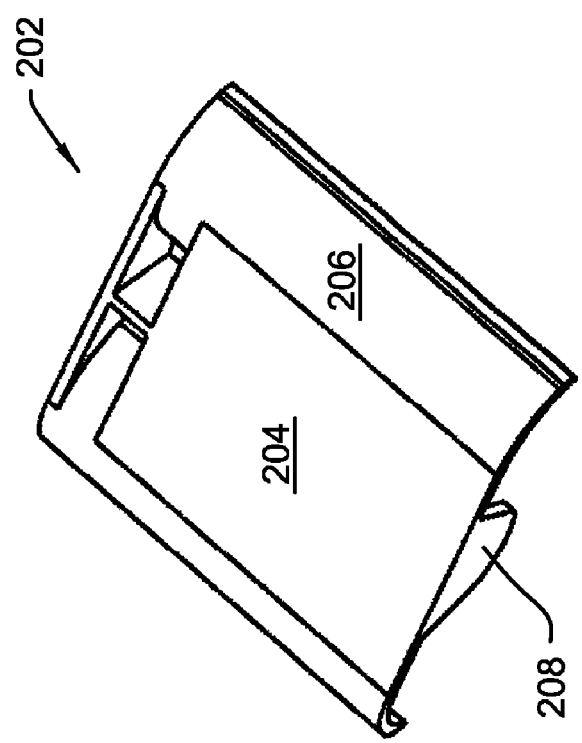
FIG. 15 is a top perspective view of the bottom plate of the battery pack.

A back plate 202 is disposed over the rear end of the cell cluster. The back plate 202, now described by reference to FIGS. 15 and 16, has a base 204. Inwardly curved wings 206 extend from the sides of the base. When the battery pack 32 is assembled, each wing 206 curves over the adjacent cell 36 of the adjacent end row of cells. The back plane is further formed to have a number of longitudinally spaced apart, convex ribs that extend inwardly from the inner surface of plate base 204. In the illustrated version of the invention, there is a single rib 208 at one end of the back plate with a relatively thick depth. Spaced from rib 208 are plural additional ribs 210 each with a thickness less than that of rib 208. Ribs 208 and 210 are all parallel.

In some versions of the invention, adhesives hold the front plate 168 and back plate 202 to the cell cluster.

A shrink wrap tube 212 forms an insulating cover around the cells 36. In FIG. 12, the shrink wrap tube 212 is shown generally in its shrunken shape. Thus, when the tube 212 is so shrunk, it extends over the wings 172 and 206 of, respectively, the front plate 168 and back plate 202.

In many versions of the invention, a small handle (not illustrated) extends an outer side surface of the battery pack 34. The handle facilitates the insertion and removal of the battery pack 34 from the housing 32. This handle may be attached to either the front plate 168 or the back plate 202. The handle is pivotally attached to the battery pack component to which it, the handle, is attached. This construction allows the handle to lie flat against the battery pack 34, when the pack 34 is removably sealed in the housing 32.

Battery assembly 30 of this invention is prepared for use by charging the battery pack 34. The battery pack 34 is charged using the same protocol in which a battery assembly with an integral cell cluster is charged; battery pack head 48 is fitted into the socket of a complementary charger. Since battery pack head 48 has the same basic geometric features of the housing head 46, the cell pack 34 can be charged using the same socket that would normally be used to charge the battery if the cells were integral with the housing 32.

During the charging process, the charger can, if necessary, exchange data with and receive charging instructions from microcontroller 182. The charger also obtains signals from the temperature sensor 184. These signals represent the temperature of the cells 36. The signal exchange from the microcontroller 182, which also provides the signals from temperature sensor, is over the one-wire connection established between communications contact 190 and a complementary contact part of the charger.

To prepare battery assembly 30 for use in an aseptic environment, housing 32 is sterilized. By "sterile," it is meant that, once the process is complete, the housing 32 has a sterilization assurance level (SAL) of at least $10^{-6}$. This means that there is equal to or less than one chance in a million that a single viable microorganism is present on the sterilized item. This definition of sterile is the definition set forth in the ANSI/AAMI ST35-1966, Safe handling and biological decontaminiation of medical devices in health care facilities and nonclinical settings. For alternative applications, the "sterilization" process is sufficient if, once the process is complete, the housing 32 has an SAL of at least $10^{-4}$.

Any one of a number of different processes can be used to sterilize the housing. A steam process, wherein the housing 32 is subjected to a flash, Hi-vac or gravity steam sterilization may be employed. Alternatively, housing 32 may be placed in a chamber and exposed to a sterilant gas. One such process involves exposing the process to ethylene oxide (ETO). Other processes employ gaseous hydrogen peroxide as the sterilant gas. One such sterilization process is sold under the trademark STERRAD by Johnson and Johnson Company of New Brunswick, N.J. Alternatively, a plasma process is used to sterilize the housing 32. In a plasma process the housing is exposed to ionized gas that performs the sterilization. The foregoing list should not be interpreted as all inclusive. Other processes may be performed to sterilize the battery. It should be recognized that exposure to the sterilization process does not, other than normal environmental exposure, degrade the performance of the components forming the housing 32.

Battery pack 34 can be charged simultaneously with the sterilization of the housing. Battery pack 34, it is understood is not sterilized and is typically not sterilizable.

Figure 17:
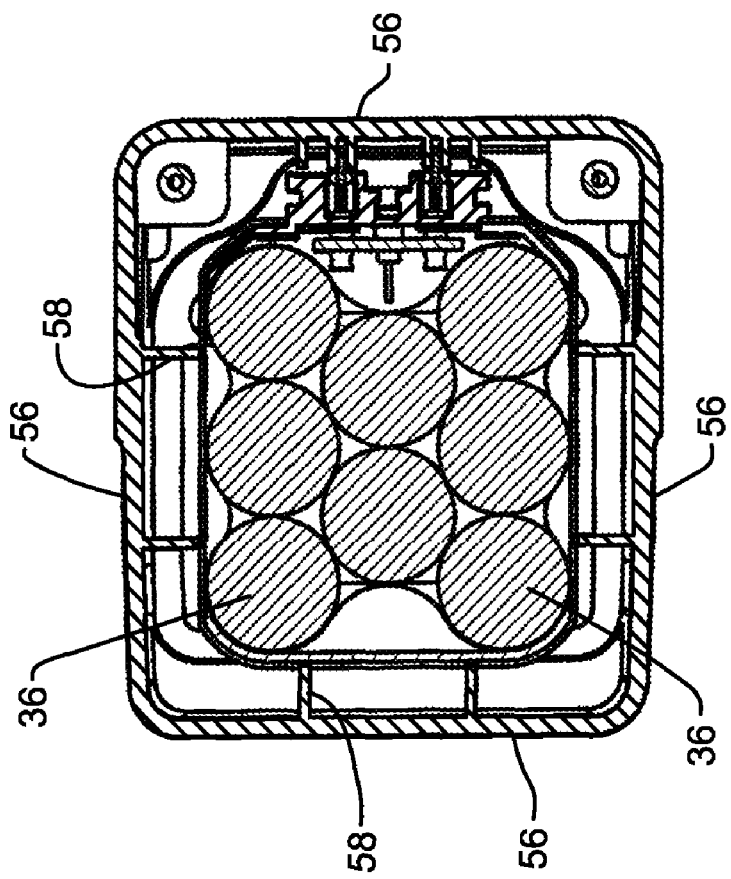
FIG. 17 is cross sectional view of the battery assembly, in the horizontal plane.

Once housing 32 is sterilized and the battery pack 34 charged, the pack is placed in the housing. Typically, the battery pack 34 is inserted into the housing chamber 38 through a sterile transfer shield (not illustrated). This ensures the non-sterile surfaces of the pack 34 do not contact the sterile surfaces of the housing 32. In this step, the battery pack 34 is fit in the open chamber 38 so that pack head 48 faces the housing blade contacts 50. As a consequence of the slide of the battery pack 34 into the housing chamber 38, each blade contact 50 seats between the opposed legs of one of the battery pack external contact 186 as seen best in FIGS. 17 and 18.

Once the battery pack 34 is seated in the housing chamber 38, the cover 40 is closed. As a consequence of the pivoting of the cover 40 against the open end of the housing body 54, seal 104 is compressed between the inner corners of the housing panels 56, the cover 40 and the retainer 108. As a consequence of this compression, seen in detail in FIG. 11, seal 104 essentially forms a hermetic barrier between the cover and the housing body 54.

Battery assembly 30 is thus ready for use. Blade contacts 50 establish a connection between the charged cells 36 and the external housing contacts 82. Contaminates that may be present on the battery pack 34 are contained within the sealed housing chamber 38.

Battery assembly 30 of this invention thus provides a means for charging a power consuming device wherein the cells 36 providing the energy are contained in a sterile housing 32. Therefore, assembly 30 can be used to provide power at locations wherein the battery needs to be aseptic, for example, the sterile field of an operating room. Since the cell-containing battery pack 34 is not autoclaved, the cells 36 are not exposed to the degradation caused by this process.

As seen by FIG. 19, another feature of battery assembly 30 is that the battery pack head 48 has geometric features that allow it to be seated in the charger socket 226 shaped to receive the head of conventional battery 224. In FIG. 19, a charger 222 is shown is having four sockets 226 so that plural batteries can be simultaneously charged. Battery 224 is a sterilizable battery. This means that battery 224 can, like housing 32, be subjected to a process that leaves the battery sterile and that the single exposure to such a process will not appreciably degrade battery performance. Battery 224 has a head 228, shown downwardly facing in FIG. 19. Battery head 228 is dimensioned to be received in one of the sockets 226. When the battery head 228 is so seated, charger contacts 230, (one shown) that project into the socket 226, abut complementary contacts in the battery head (battery head contacts not illustrated).

Charging current is applied to the battery across these interfaces. Many batteries 224 are further designed so their heads 228 further function as their structural members, that, like housing head 46 (FIG. 1), are coupled to the power consuming device. To this end battery head 228, like housing head 46, has a latch 232 that removably holds the battery 224 and more particularly the head 228, to the power consuming device. Thus, with this type of battery, the contacts internal to the head also function as the contacts over which power is supplied to the power consuming device. It should be appreciated that an alternative sterilizable battery may have a second head and/or a second set of contacts for establishing, respectively, mechanical and electrical connections to the power consuming device.

Since battery pack head 48 fits in the same socket 226 shaped to received head 228 of the sterilzable battery 224, the requirement for the supplier of the charger to make available chargers or charger modules with different shaped sockets; one to accommodate a sterlizable battery assembly with cells sealed therein and a second one to accommodate battery pack 34, is eliminated.

Battery housing 32 is constructed so that when the cover 40 is closed, seal 104 is compressed between the cover components and inner edges 61 of the housing-forming panels 56. This arrangement eliminates the need to construct the housing body 54 so that the bases of panels are of sufficient width to function as the surfaces against which the seal seats. Instead, the housing panels can be made to have relatively narrow open ends. In some versions of the invention, this width, which is the thickness of the panels, is 0.150 inches or less. The minimization of the thickness of these structural components helps to keep the overall size and weight of the battery assembly 30 to a minimum.

The latch assembly of this invention is designed so that spring 136 performs two functions. First, the spring holds the latch 44 in the locked position. Secondly spring 136 serves as the component that pivotally holds the associated latch 44 to the housing. This arrangement helps reduce the number of components required to construct the battery assembly 30 of this invention.

It should be understood that the foregoing is directed to one specific version of the invention. Other versions of the invention may have alternative features. For example, there is no requirement that all versions of the battery assembly be provided with the battery pack head geometry, the seal arrangement or the disclosed latch assembly.

In some versions of the invention the battery pack 34 may even be included with structural and geometric features to allow it, outside of the housing 32 to be attached to a device the pack is intended to power.

There is no requirement that, in all versions of the invention, blade contacts function as the conductive members internal to the battery housing 32 that establish electrical connections to the battery pack external contacts 186.

Similarly, housing 32 may be of a construction different from what has been described. The disclosed and illustrated geometric features are understood to be exemplary, not limiting. For example, in some versions of the invention, the housing is formed to have a flange that extends completely circumferentially around the opening into housing chamber 38. Some of the parts of the housing, such as the cover 40, may be formed from metal. There is no requirement that in all versions of the invention that the lid 64 be welded to the housing body 54. In some versions of the invention, fasteners may be employed to accomplish the mating of these two components.

Similarly, in some versions of the invention the cover may be removable. The cover 40 may slidably be fitted to the housing 32. Likewise, in an alternative version of the invention, the two spaced apart leaves for receiving the hinge pins 98 may be formed on the cover. In these versions of the invention, the battery housing 32 is formed to have the complementary single boss for receiving the free ends of the hinge pins 98.

Further, in some version of the invention, the cover may be formed with a groove or other geometric feature for receiving the complementary seal. This would make it possible to press-fit secure or otherwise mount the seal to the cover without requiring a supplemental seal retainer or other fastening component.

There is likewise no requirement that, in all versions of the invention, a single component be both to hold each latch 44 in place and bias the latch in the locked position. For example, in some versions of the invention, a retaining member is used to hold each latch to the housing 32 and a second member is used to bias the latch in the locked position. This second member may be spring or sterilizable foam. In this type of assembly, the fastener that holds the latch in position, the fastener fitted to the retaining member, may even be positioned to extend into a bore adjacent the open bottom end of the housing 32.

The latch geometry may be different in order to provide either a more secure latch or a housing assembly with a more aesthetically pleasing appearance.

Battery housing 32 may also be provided with alternative internal contacts. Thus, in some versions of the invention each internal contact may be provided with an opening for receiving a fastener that holds the contact to the housing 32. In these versions of the invention, it may be necessary to shape the blades to have different sections that are not coplanar. Thus, a housing internal contact may have a first section dimensioned to contact the complementary battery pack contact 186, a second section formed to receive a fastening element and a third section formed to receive a conductor to facilitate the connection to the associated housing external contact 82. These different sections may be in different planes so as give the internal contact an overall shape that is not flat.

In versions of the invention wherein supplemental fasteners hold the internal contacts to the battery housing 32, one or more of the reinforcing webs 90 can be fully or partially eliminated.

Also, in some versions of the invention, it may be desirable to provide the battery housing 32 with additional components so a conductive link can be established through the housing with the battery pack communications contact 190. In these versions of the invention, battery housing 32 is provided with a third internal contact positioned to abut the communications contact 190. Housing head 46 is provided with a third external contact to which the internal contact is connected.

One reason it is desirable to provide the above connections is that some cordless powered surgical tools write data to the memory of the battery employed to power the tool. The above arrangement allows such signal transfer. Also, there may be times when it is desirable to provide the battery housing 32 with a microcontroller or at least a memory. This type of component makes it possible to store in the battery housing 32 data regarding the autoclave history and use history of the housing. Such data is desirable if, for example, there is concern that a larger number of autoclavings or an excessively long autoclaving could adversely affect the integrity of the seal. In these versions of the invention, the housing microcontroller or memory and potentially complementary temperature sensor is disposed on a circuit board mounted to the undersurface of the lid. In some versions of the invention, the housing internal contact that connects to the battery pack communications contact 190 is connected to this circuit board. In these versions of the invention, the individual battery housing and battery pack data storage component, memory or microcontroller, are attached to a common one-wire bus.

Alternatively, there may be reasons, such as economic, where the two data storage components are not connected. In these versions of the invention, the housing may not include an internal contact to the battery pack communications contact 190.

Likewise, it should be understood that the actual geometries of the housing head 46 and battery pack head 48 are exemplary, not limiting. Further in some versions of the invention it may be possible to design the battery so there is a single external housing contact, a single housing internal contact and a single battery pack contact.

Alternative structures of the seal may be appropriate in some versions of the invention. In some versions of the invention, the seal may be mounted to the housing body 54 such that when the cover 40 is positioned to enclose the chamber, the cover presses against the seal.

Similarly, in some versions of the invention, it may be desirable to mount the latch that holds the cover 40 closed to the cover.

The structure of the battery pack 32 is also exemplary, not limiting. In other versions of the invention, a component other than a section of shrink wrap tubing can function as the structural component that forms the outer shell of the battery pack 34. In some versions of the invention, the battery pack includes its own rigid housing that forms both the head and base of the battery pack. An advantage of these versions of the invention is that the rigid housing provides additional protection for the rechargeable cells 36. In these versions of the invention, there is no requirement that the cells 36 be contained in shrink wrap envelop. Similarly, in these versions of the invention, as well as other versions of the invention, it may not be necessary to user the binders, other structural components or adhesives to hold the cells together so that they form a unitary cluster. Alternatively, one or more sections of adhesive tape can serve as the component/components that holds/hold the battery pack together.

Further, it should be appreciated that, in some versions of the invention, battery pack 34 is shaped so that it has a head that fits in charger socket 226, the contacts integral with the battery pack may not physically abut the contacts 230 that establish electrical connection to the sterilizable battery 224. Thus, in some versions of the invention, two sets of contacts may be mounted to the structural components of the charger 222 that form the socket 226. In these assemblies, the contacts integral with the sterilizable battery 224 abut a first set of charger contacts. The contacts integral with battery pack 34 abut a second set of charger contacts. In still another variation of this invention, the battery pack head 48 is dimensioned to be received in the charger socket 226. More particularly, in this version of this invention, a removable module, (not illustrated) is also disposed in the charger socket 224. This module has mechanical or conductive features for, respectively, holding the battery in the socket or establishing an electrical connection between the battery pack contacts 186 and the charger contacts 230.

Similarly, in some versions of the invention, the battery pack may have two sets of contacts. A first set of contacts serves as the conductive members through which charge is stored in the cells 36. A second set of contacts serves as the contacts that abut the contacts 50 internal to the battery housing 32. The contacts in this second set of contacts thus serve as the conductive members through which charge is drawn from cells 36.

Likewise, in the illustrated version of the invention, housing head 46 can be fitted in charger socket 226 in which the sterilizable battery 224 is fitted. It should be appreciated that the invention is not so limited to this feature. In other versions of the invention, the battery pack 32 may be constructed so that its head 46 can only be fitted to the power consuming device battery assembly 30 is intended to power.

In some versions of the invention, the battery pack 34 may be formed from components that allow the battery pack to withstand sterilization. In some of these versions of the invention, the battery pack 34 may be sterilizable, but to a lesser extent than to which housing 32 is sterilizable.

Also, in the described version of the invention other than cover 40, no device holds the battery pack 34 in the housing chamber 38. In alternative versions of the invention, a latch mechanism may perform this function. The moving components of the latch can be attached to either the housing 32 or the battery pack 34. The inclusion of the latch may eliminate the need to provide the cover.

Therefore, it is an object of the appended claims to cover all such variations and modifications as come within the true spirit and scope of the invention.

What is claimed is:

1. A method of charging and using an aseptic battery, said method including the steps of:
    providing a charger with a socket, the socket shaped to receive a sterilizable battery that has at least one rechargeable cell, the socket having terminals across which a charging current is applied to the at least one rechargeable cell of the sterilizable battery;
    fitting to the charger socket shaped to receive a sterilzable battery a non-sterilizable battery pack that has at least one rechargeable cell;
    with the charger, charging the at least one rechargeable cell of the non-sterilizable battery pack;
    after said charging of the at least one rechargeable cell of the battery pack, placing the battery pack in a sterilizable housing that has been sterilized, the housing have a head with external contacts and internal contacts located in the housing, the internal contacts being electrically connected to the external contacts wherein, as a result of the said placement of the battery pack in the housing, the battery pack at least one rechargeable cell is placed in contact with the housing internal contacts, and enclosing the battery pack in the housing;
    after said enclosing the battery pack in the sterilizable housing, connecting the housing head to a surgical tool; and
    providing power to the surgical tool from the battery pack at least one rechargeable cell through the housing internal and external contacts.

2. The method of charging and using an aseptic battery of claim 1, wherein:
    the battery pack has at least one external contact that is connected to the at least one rechargeable cell of the battery pack;
    in said step of fitting the battery pack to the charger socket, the battery pack is fitted to the socket so that the battery pack external contact contacts a terminal to which contacts integral with the sterilizable battery would contact, so that, in said charging step, the charger charges the battery pack at least one rechargeable cell through the terminal over which current would be applied to the at least one rechargeable cell of the sterilizable battery; and in said step of placing the battery pack in the sterilizable housing, the battery pack is positioned so that the at least one external contact of the battery pack abuts one of the internal contacts of the sterilizable housing so that, in said step of providing power to the surgical tool, power is provided from the at least one rechargeable cell of the battery pack through the at least one external contact of the battery pack, at least one of the internal contacts of the sterilizable housing and at least one of the external contacts of the sterilizable housing.

3. The method of charging and using an aseptic battery of claim 2, wherein:

the battery pack has a plurality of external contacts connected to the at least one rechargeable cell of the battery pack;

in said step of placing the battery pack in the sterilizable housing, the battery pack is positioned so that the external contacts of the battery pack abut separate ones of the internal contacts of the sterilizable housing so that, in said step of providing power to the surgical tool, power is provided from the at least one rechargeable cell of the battery pack through the external contacts of the battery pack, the internal contacts of the sterilizable housing and the external contacts of the sterilizable housing.

4. The method of charging and using an aseptic battery of claim 1, wherein:

a lid is moveably attached to said sterilizable housing so that when the sterilizable housing is subjected to a sterilization process, the lid is sterilized; and in said step of enclosing the battery pack in the sterilizable housing, the lid is moved so as to be positioned over the battery pack and is latched to the sterilizable housing.

5. The method of charging and using an aseptic battery of claim 1, wherein, in said step of enclosing the battery pack in the sterilized housing, a cover is secured over the battery pack and the sterilizable housing, a seal is positioned between the cover and the sterilizable pack so that when the cover is secured over the sterilizable housing, the seal is compressed between the cover and the sterilizable housing.

6. The method of charging and using an aseptic battery of claim 1, wherein:

the battery pack includes a memory and a communications contact that is connected to the battery memory and the sterilizable housing includes an internal data contact disposed in the housing and an external data contact located outside of the housing, the internal and external data contacts being connected together;

as a result of said placement of the battery pack in the sterilizable housing, a conductive link is established between the battery pack communications contact and the internal data contact of the sterilizable housing; and after said step of connecting the sterilizable housing to the surgical tool, further including the step of writing data from the surgical tool through the sterilizable housing external and internal data contacts and the battery pack communications contact to the battery pack memory.

7. The method of charging an aseptic battery of claim 1, wherein the sterilizable housing is sterilized to a sterilization assurance level of at least $10^{-4}$.

8. A method of charging and using an aseptic battery, said method including the steps of:

providing a charger with a socket, the socket shaped to receive a sterilizable battery that has at least one rechargeable cell, the socket having terminals across which a charging current is applied to the at least one rechargeable cell of the sterilizable battery;

seating a battery pack that is not sterilizable in the charger socket, the battery pack having at least one rechargeable cell and power contacts that are connected to the at least one cell, wherein in said step of seating the battery pack, the battery pack power contacts are electrically connected to the socket terminals;

charging the at least one rechargeable cell of the battery pack by applying a charging current through the socket terminals and the battery pack power contacts to the cell;

after said step of charging the at least one rechargeable cell of the battery pack, placing the battery pack in a previously sterilized housing, the housing having: a void space in which the battery pack is placed; internal power contacts located in the void space; and external power contacts located outside of the housing that are connected to the internal power contacts wherein, as a result of said step of placing the battery pack in the sterilized housing, electrical connections are established between the battery pack power contacts and the housing internal power contacts;

with a sterilized cover, enclosing the battery pack in the sterilized housing;

connecting the sterilized housing to a surgical tool so that, as a result of said connection step, the housing external power contacts are conductively connected to power contacts integral with the surgical tool; and providing power to the surgical tool from the battery pack at least one rechargeable cell through the battery pack power contacts, the internal and external power contacts of the sterilized housing and the surgical tool power contacts integral with the surgical tool.

9. The method of charging and using an aseptic battery of claim 8, wherein, in said step of enclosing the battery pack in the sterilized housing, a lid that is moveably attached to housing so that the lid is sterilized with housing so as to function as the sterilized cover is closed over the battery pack.

10. The method of charging and using an aseptic battery of claim 8, wherein, in said step of enclosing the battery pack in the sterilized housing, a seal is compressed between the sterilized cover and sections of the sterilized housing.

11. The method of charging and using an aseptic battery of claim 8, wherein:

the battery pack includes a memory and a communications contact that is connected to the battery memory and the sterilized housing includes an internal data contact disposed in the housing and an external data contact located outside of the housing, the internal and external data contacts being connected together;

as a result of said placement of the battery pack in the sterilized housing, a conductive link is established between the battery pack communications contact and the internal data contact of the sterilized housing; and after said step of connecting the sterilizable housing to the surgical tool, writing data from the surgical tool through the sterilized housing external and internal data contacts and the battery pack communications contact to the battery pack memory.

12. The method of charging an aseptic battery of claim 8, wherein the sterilized housing is sterilized to a sterilization assurance level of at least $10^{-4}$.

* * * * *